US010876143B2

(12) United States Patent
Swarts et al.

(10) Patent No.: US 10,876,143 B2
(45) Date of Patent: Dec. 29, 2020

(54) CHEMOENZYMATIC SYNTHESIS OF TREHALOSE ANALOGS

(71) Applicants: Central Michigan University, Mount Pleasant, MI (US); University of Maine System, Bangor, ME (US)

(72) Inventors: Benjamin M. Swarts, Mount Pleasant, MI (US); Peter Woodruff, Portland, ME (US)

(73) Assignees: Central Michigan University, Mount Pleasant, MI (US); University of Maine System, Bangor, ME (US)

( * ) Notice: Subject to any disclaimer, the term of this patent is extended or adjusted under 35 U.S.C. 154(b) by 0 days.

(21) Appl. No.: 15/845,555

(22) Filed: Dec. 18, 2017

(65) Prior Publication Data

US 2018/0119196 A1   May 3, 2018

Related U.S. Application Data

(63) Continuation of application No. 14/641,007, filed on Mar. 6, 2015, now Pat. No. 9,873,905.

(60) Provisional application No. 61/949,688, filed on Mar. 7, 2014.

(51) Int. Cl.
| | |
|---|---|
| *C12Q 1/04* | (2006.01) |
| *C12P 19/12* | (2006.01) |
| *C07H 3/04* | (2006.01) |
| *C07H 1/00* | (2006.01) |

(52) U.S. Cl.
CPC .......... *C12Q 1/04* (2013.01); *C07H 1/00* (2013.01); *C07H 3/04* (2013.01); *C12P 19/12* (2013.01); *G01N 2333/35* (2013.01); *G01N 2333/91102* (2013.01); *G01N 2400/14* (2013.01)

(58) Field of Classification Search
CPC .......... A61K 2300/00; A61K 31/445; A61K 31/7016; A61K 31/4375; A61K 45/06; A61K 9/0053; A61K 31/216; A61K 49/0043; A61K 49/0067; C07H 3/04; C07H 7/06; C07H 11/04; C07H 13/06; C07H 5/02; C07H 1/00; G01N 21/78; G01N 2800/04; G01N 33/84; G01N 2333/35; G01N 2333/91102; G01N 2400/14; G01N 27/327; G01N 27/3275; G01N 33/4925; G01N 33/6893; G01N 2333/986; G01N 2800/26; G01N 2021/775; G01N 2021/7759; G01N 33/6806; G01N 33/582; G01N 33/60; C12P 19/12; C12Q 1/04; C12Q 1/34; C12Q 1/16; C07D 501/24; C07D 501/26; C07D 501/30; C07D 501/34; C07D 501/57; A61P 3/00; B01L 2200/16; B01L 2300/0636; B01L 3/502715
See application file for complete search history.

(56) References Cited

U.S. PATENT DOCUMENTS

| | | | |
|---|---|---|---|
| 8,481,026 B1 * | 7/2013 | Woodruff | B09C 1/10 424/241.1 |
| 9,677,112 B2 * | 6/2017 | Rao | C07D 501/24 |
| 2012/0263649 A1 * | 10/2012 | Backus | A61K 49/0043 424/9.1 |
| 2013/0302857 A1 | 11/2013 | Van Der Borght et al. | |
| 2014/0051599 A1 | 2/2014 | Gwenin | |
| 2015/0125884 A1 | 5/2015 | Budin et al. | |
| 2015/0252402 A1 | 9/2015 | Swarts et al. | |

FOREIGN PATENT DOCUMENTS

WO    2011030160    3/2011

OTHER PUBLICATIONS

Abanyo, M. & Taylor, N.F. Biosci Rep (1986) 6: 309. https//doi. org/10.1007/BF01115160, Abstract Only. (Year: 1986).*
Woodruff et al, "Trehalose Is Required for Growth of *Mycobacterium smegmatis*" J. of Biol. Biochem., vol. 279 No. 28, pp. 28835-28843. (Year: 2004).*
Brand et al., "Covenient Preparative Synthesis of [14C]Trehalose from [14C]Glucose by Intact *Escherichia coli* Cells," Applied and Environmental Microbiology, 1989, 55(9):2414-2415.
Garcia et al., "Syntheses of hepta-, hexa-, and penta-pivalates of trehalose by selective pivaloylation," Carbohydrate Research, 1990, 200:307-317.
Lin et al., "Synthesis of mono- and dideoxygenated α,α-trehalose analogs," Carbohydr Res, 2007, 342(14):2014-2030.
Peña-Zalbidea et al., "Chemoenzymatic radiosynthesis of 2-deoxy-2[18F]fluoro-D-trehalose ([18F]-2-FDTre): A PET radioprobe for in vivo tracing of trehalose metabolism," Carbohydrate Research, 2019, 472:16-22.
Rundell et al., "Deoxyfluoro-D-trehalose (FDTre) analoges as potential PET probes for imaging mycobacterial infection," Organic & Biomolecular Chemistry, 2016, 12 pages.
Aisaka et al., "Enzymatic synthesis of novel disaccharides using disaccharide phosphorylases," J. Biosci. Bioeng., 2000, vol. 90, 208-213.
Backus et al., "Uptake of unnatural trehalose analogs as a reporter for *Mycobacterium tuberculosis*," Nat. Chem. Biol., 2011, vol. 7, 228-235.
Belisle et al., "Role of the major antigen of *Mycobacterium tuberculosis* in cell wall biogenesis," Science, 1997, 276, 1420-2.
Belocopitow et al., "Enzymic synthesis of 6-deoxy-α-D-glucopyranosyl α-D-glucopyranoside and α-D-xylopyranosyl α-D-glucopyranoside," Carbohydr. Res., 1971, vol. 19, pp. 268-271.
Breidenbach et al., "Targeted metabolic labeling of yeast N-glycans with unnatural sugars," Proc. Natl. Acad. Sci. U.S.A., 2010, 107, 3988-3993.
Brennan et al., "The envelope of mycobacteria," Annu. Rev. Biochem., 1995, 64, 29-63.

(Continued)

*Primary Examiner* — Deborah K Ware
(74) *Attorney, Agent, or Firm* — Michael Best & Freidrich LLP

(57) ABSTRACT

The present invention provides methods of synthesizing trehalose analogues; methods of detecting mycobacteria, and trehalose analogues.

7 Claims, 11 Drawing Sheets

Specification includes a Sequence Listing.

(56) References Cited

OTHER PUBLICATIONS

Chaen et al.,"Efficient Enzymatic Synthesis of Disaccharide, α-D-Galactosyl α-D-Glucoside, by Trehalose Phosphorylase from Thermoanaerobacter brockii," J. Appl. Glycosci., 2001, vol. 48, pp. 135-137.

Elbein et al., "New insights on trehalose: a multifunctional molecule," Glycobiology, 2003, 13, 17R-27R.

Foley et al., "Bioorthogonal Chemical Reporters for Selective In Situ Probing of Mycomemembrane Components in Mycobacteria," Angew Chem Int Ed Engl. Feb. 5, 2016;55(6):2053-7.

Gobec et al., "Design, synthesis, biochemical evaluation and antimycobacterial action of phosphonate inhibitors of antigen 85C, a crucial enzyme involved in biosynthesis of the mycobacterial cell wall," Eur. J. Med. Chem., 2007, 42, 54.

Grzegorzewicz et al., "Inhibition of mycolic acid transport across the *Mycobacterium tuberculosis* plasma membrane," Nat. Chem. Biol., 2012, 19, 334-41.

Haberkant et al., In vivo profiling and visualization of cellular protein-lipid interactions using bifunctional fatty acids, Angew Chem Int Ed 2013, 52:4033-4038.

Kalscheuer et al.,"Trehalose-recycling ABC transporter LpqY-SugA-SugB-SugC is essential for virulence of *Mycobacterium tuberculosis*," Proc. Natl. Acad. Sci. U.S.A., 2010, 107, 21761-66.

Kim et al., "Enzymatic synthesis of a galactose-containing trehalose analogue disaccharide by Pyrococcus horikoshii trehalose-synthesizing glycosyltransferase: Inhibitory effects on several disaccharidase activities," Journal of Molecular Catalysis B: Enzymatic 49, 2007, 98-103.

Kouril et al., "A novel trehalose synthesizing pathway in the hyperthermophilic Crenarchaeon Thermoproteus tenax: the unidirectional TreT pathway," Arch Microbiol, 2008, 190:355-369.

La Rosa et al., "MmpL3 Is the Cellular Target of the Antitubercular Pyrrole Derivative BM212," Antimicrob. Agents Chemother., 2012, 56, 324-331.

Marrakchi et al., "Mycolic acids: structures, biosynthesis, and beyond," Chem. Biol., 2013, 21, 67-85.

Maruta et al., "Formation of Trehalose from Maltooligosaccharides by a Novel Enzymatic System," Biosci. Thotechnol. Biochem., 1995, vol. 59, pp. 1829-1834.

Ohtake et al., "Trehalose: Current Use and Future Applications," J. Pharm. Sci., 2011, vol. 100, pp. 2020-2053.

Rose et al., "Synthesis and biological evaluation of trehalose analogs as potential inhibitors of mycobacterial cell wall biosynthesis," Carbohydr. Res., 2002, 337, 105-20.

Rostovtsev et al., "A stepwise huisgen cycloaddition process: copper(I)-catalyzed regioselective "ligation" of azides and terminal alkynes," Angew. Chem. Int. Ed., 2002, 41, 2596-9.

Ryu et al., "Molecular cloning and characterization of trehalose synthase from Thermotoga maritima DSM3109: Syntheses of trehalose disaccharide analogues and NDP-glucoses," Enzyme and Microbial Technology 47, 2010, 249-256.

Sarpe et al., "Regioselective Protection and Functionalization of Trehalose," Trends in Carbohydrate Research, 2013, vol. 5, pp. 8-33.

Stanley et al., "Identification of Novel Inhibitors of *M. tuberculosis* Growth Using Whole Cell Based High-Throughput Screening," ACS Chem. Biol., 2012, 7, 1377-84.

Swarts et al.,Probing the mycobacterial trehalome with bioorthogonal chemistry, J. Am. Chem. Soc., 2012, vol. 134, pp. 16123-16126.

Tornøe et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem., 2002, 67, 3057-64.

Tournu et al., "Relevance of Trehalose in Pathogenicity: Some General Rules, Yet Many Exceptions," Pathog., 2013, 9, e1003447.

Van Der Borght et al., "Enzymatic Properties and Substrate Specificity of the Trehalose Phosphorylase from Caldanaerobacter subterraneus," Appl. Environ. Microbiol., 2011, vol. 77, 6939-6944.

Wang et al., "Synthesis of trehalose-based compounds and their inhibitory activities against *Mycobacterium smegmatis*," Bioorg. Med. Chem., 2004, 12, 6397-413.

Walmagh et al., "Trehalose Analogues: Latest insights in properties and biocatalytic production," Int J Mol Sci, 2015, 16, 13729-45.

Asensio et al. "The virulence-associated two-component PhoP-PhoR system controls the biosynthesis of polyketide-derived lipids in *Mycobacterium tuberculosis*." Journal of Biological Chemistry. Jan. 20, 2006;281(3):1313-6.

United States Patent Office Action for U.S. Appl. No. 15/701,084 dated Feb. 15, 2019, 10 pages.

Urbanek et al., "Chemoenzymatic Synthesis of Trehalose Analogues: RapidAccess to Chemical Probes for Investigating Mycobacteria," ChemBioChem, 2014, 15(14):2066-70.

* cited by examiner

FIG. 1A

| Entry | Substrate | Product | Yield (%)ᵃ |
|---|---|---|---|
| 1 | Glc | Tre | > 99 |
| 2 | 2-FluoroGlc | 2-FluoroTre | > 99 |
| 3 | 2-DeoxyGlc | 2-DeoxyTre | > 99 |
| 4 | 2-GlcAz | 2-TreAz | N.D. |
| 5 | Mannose | α,α-ManGlc | 87 |
| 6 | 3-FluoroGlc | 3-FluoroTre | > 99 |

| Entry | Substrate | Product | Yield (%)[a] |
|---|---|---|---|
| 7 |  3-DeoxyGlc |  3-DeoxyTre | 75 |
| 8 |  3-GlcAz |  3-TreAz | 95 |
| 9 |  Allose |  α,α-AllGlc | N.D. |
| 10 |  4-FluoroGlc |  4-FluoroTre | 7 |
| 11 |  4-DeoxyGlc |  4-DeoxyTre | 26 |
| 12 |  4-GlcAz |  4-TreAz | N.D. |

FIG. 1C

| Entry | Substrate | Product | Yield (%)$^a$ |
|---|---|---|---|
| 13 | Galactose | α,α-GalGlc | 12 |
| 14 | 6-FluoroGlc | 6-FluoroTre | 98 |
| 15 | 6-DeoxyGlc | 6-DeoxyTre | 87 |
| 16 | 6-GlcAz | 6-TreAz | > 99 |

FIG. 1D

| Entry | Substrate | Product | Yield (%)[a] |
|---|---|---|---|
| 17 | 5-ThioGlc | 5-ThioTre | > 99 |

[a]Yields determined by HPLC. N.D., not detected.

CHEMOENZYMATIC SYNTHESIS OF TREHALOSE ANALOGS

CROSS-REFERENCE TO RELATED APPLICATIONS

This application is a continuation of U.S. Utility patent application Ser. No. 14/641,007, filed Mar. 6, 2015, which claims priority to U.S. Provisional Patent Application No. 61/949,688, filed Mar. 7, 2014, the contents of which are hereby incorporated herein by reference in their entirety.

STATEMENT OF GOVERNMENT INTEREST

This invention was made with government support under grant number R15 AI117670 awarded by the National Institutes of Health. The government has certain rights in the invention.

BACKGROUND

Trehalose is a $C_2$-symmetric disaccharide consisting of two glucose molecules linked together by a 1,1-α,α-glycosidic bond. Although trehalose is not present in mammals, it is widespread elsewhere in nature, where it primarily functions as an energy source and as a protectant against desiccation, osmotic stress, and changes in temperature. Trehalose metabolism is required for virulence in a number of pathogenic organisms, most notably *Mycobacterium tuberculosis* (Mtb), which is the causative agent of human *tuberculosis* (TB). Mtb is characterized by its complex cell envelope, which harbors a variety of trehalose glycolipids that are involved in cell-wall biosynthesis and that contribute to pathogenesis. The essentiality of trehalose metabolism in Mtb coupled with its absence in humans—makes it an attractive target for drug and diagnostic development, a notion that is underscored by the recent identification of numerous antimycobacterial compounds that inhibit trehalose glycolipid transport.

Despite their potential value, the development and application of trehalose analogues in TB research remains limited, in large part due to the difficulties associated with their chemical synthesis. Specifically, the $C_2$-symmetry and 1,1-α,α-glycosidic bond of trehalose pose significant challenges. Methods for the desymmetrization and regioselective hydroxyl group manipulation of trehalose are usually lengthy and low-yielding. On the other hand, methods for the formation of 1,1-α,α-glycosidic linkages are either laborious or suffer from low stereoselectivity. In addition to these technical obstacles, multi-step chemical synthesis of carbohydrates is often inefficient and inaccessible to non-experts.

A chemoenzymatic method for the synthesis of trehalose analogues would complement chemical methods and help to alleviate many of these problems. In general, enzymes can perform reactions with excellent regio- and stereoselectivity under mild conditions, and without the need for protection of substrate functional groups. Moreover, enzymatic reactions are easy to carry out, non-hazardous, and environmentally benign, making chemoenzymatic synthesis a cornerstone of "green" chemistry development. These attributes, coupled with the increasing focus on trehalose and its derivatives in various scientific fields, motivated us to develop a robust chemoenzymatic approach to trehalose analogue synthesis.

SUMMARY

In one embodiment, the invention provides a method for synthesizing trehalose analogues comprising contacting a glucose analogue with a trehalose synthase, a magnesium salt and a monosaccharide donor, with the provisio that either the glucose analogue is not glucose or the monosaccharide donor is not a glucose donor.

In one embodiment, the invention provides a method of detecting live mycobacteria in a sample comprising contacting a glucose analogue with a trehalose synthase, a magnesium salt and a monosaccaride donor to form a trehalose analogue; contacting a sample with the trehalose analogue; detecting the labeled mycobacteria; wherein the trehalose analogue is labeled with a detectable moiety.

In one embodiment, the invention provides a method of detecting mycobacteria in a cell comprising contacting a cell with a trehalose analogue; contacting a sample with the trehalose analogue; detecting the labeled mycobacteria; wherein the trehalose analogue is labeled with a detectable moiety; and wherein the trehalose analogue accumulates in the mycobacteria via the trehalose transport protein.

In one embodiment, the invention provides a compound according to formula (III) or (IV):

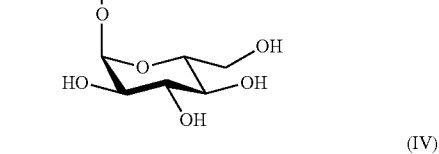

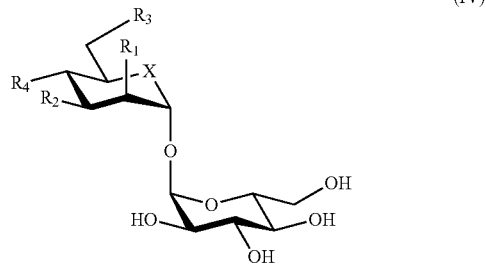

wherein
X is O, S, Se, PH, P(O)H, or P(O)OH;
$R^1$, $R^2$ and $R^3$ are independently selected from H, halo, —OR, —NR$_2$, —NR$_3^+$, —NHCOR, —SR, —SCOR, —OPO$_3^{2-}$, —SeR, —SeCOR, —N$_3$, —CN, —NC, $C_{1-6}$ alkyl, $C_{2-6}$ alkenyl, or $C_{2-6}$ alkynyl;
$R^4$ is OH, —NHR, —SH, or —SeH; and
each R is independently selected from H, $C_{1-6}$ alkyl, $C_{2-6}$ alkenyl or $C_{2-6}$ alkynyl;
with the proviso that the compound is not trehalose.

Other aspects of the invention will become apparent by consideration of the detailed description and accompanying drawings.

BRIEF DESCRIPTION OF THE DRAWINGS

FIG. 1A, FIG. 1B, FIG. 1C, and FIG. 1D show the synthesis of trehalose analogues from Glc analogues and UDP-Glc by TreT from *T. tenax*. In FIG. 1A, FIG. 1B, FIG. 1C, and FIG. 1D yields were determined by HPLC and N.D. indicates not detected.

FIG. 2A shows the experimental workflow for single-day probe synthesis, metabolic labeling, and imaging of *M. smegmatis*, and in FIG. 2B fluorescence microscopy analysis of 6-TreAz-treated (or untreated) *M. smegmatis* wild type, ΔsugC mutant, and ΔsugC::sugC complement, indicating that trehalose analogue probes can accumulate in mycobacteria via the trehalose-specific transporter SugABC-LpqY. TL, transmitted light. Scale bars, 5 μm.

FIG. 3A shows the experimental workflow for assessing uptake of fluoro-trehalose analogues by *M. smegmatis* and in FIG. 3B, FIG. 3C, FIG. 3D, and FIG. 3E gas chromatograms for analysis of fluoro-trehalose analogue uptake in *M. smegmatis* wild type, ΔsugC mutant, and ΔsugC::sugC complement, indicating that trehalose analogue probes can accumulate in mycobacteria via the trehalose-specific transporter Sug-ABC-LpqY.

DETAILED DESCRIPTION

Figure 1B:
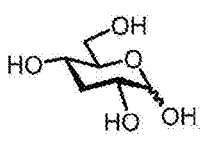
Figure 1B:
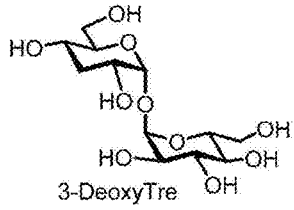
Figure 1B:
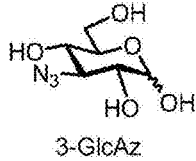
Figure 1B:
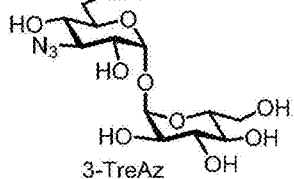
Figure 1B:
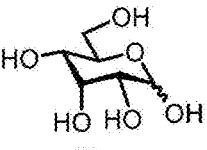
Figure 1B:
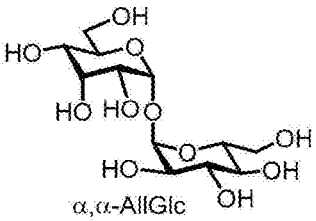
Figure 1B:
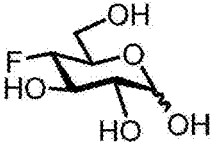
Figure 1B:
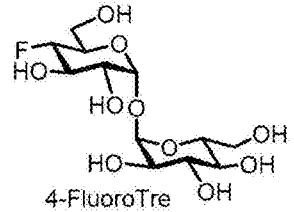
Figure 1B:
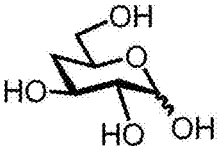
Figure 1B:
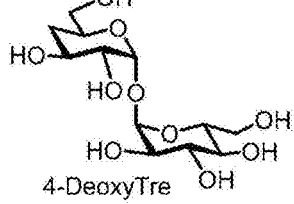
Figure 1B:
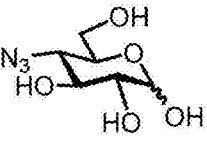
Figure 1B:
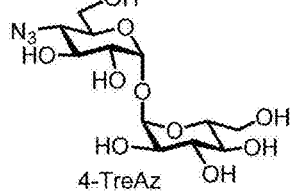

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The present invention provides chemoenzymatic methods for synthesizing trehalose analogues using a trehalose synthase (TreT) enzyme. In nature, TreT converts glucose and UDP-glucose into trehalose in a single step. The present invention uses analogues of glucose and/or UDP-glucose in the TreT reaction to generate trehalose analogues. It is expected that the methods of the present invention will be useful for rapidly and efficiently preparing trehalose analogues as potential anti-mycobacterial compounds, compounds for imaging/detection of mycobacteria, and non-degradable biopreservation/bioprotection compounds, among other applications in the biological and materials sciences. For example, these methods could be used for transforming easily accessible radiolabeled glucose analogues, e.g. [$^{14}$C]-labeled glucose or [$^{18}$F]-labeled glucose, into the corresponding [$^{14}$C]- or [$^{18}$F]-labeled trehalose analogues for investigating or imaging mycobacteria and other trehalose-containing organisms. These types of trehalose analogues are virtually inaccessible using current synthesis methods or are exceedingly expensive to purchase. The methods of the present invention will provide a simple, fast (1 hour), and high-yielding (up to 99% yield) route to synthesizing trehalose analogues for various applications.

Definitions

As used herein, the term "alkyl" refers to a branched, unbranched, or cyclic hydrocarbon having, for example, from 1 to 6 carbon atoms or from 1 to 4 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monovalent branched or unbranched partially unsaturated hydrocarbon chain (i.e. a carbon-carbon, sp$^2$ double bond). In some embodiments, an alkenyl group can have from 2 to 6 carbon atoms, or 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monovalent branched or unbranched hydrocarbon chain, having a point of complete unsaturation (i.e. a carbon-carbon, sp triple bond). In some embodiments, the alkynyl group can have from 2 to 6 carbon atoms, or 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, and the like. The alkynyl can be unsubstituted or substituted.

The term "halo" refers to fluoro, chloro, bromo, and iodo. Similarly, the term "halogen" refers to fluorine, chlorine, bromine, and iodine.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded and that the substitution results in a stable compound. Suitable indicated groups include, e.g., alkoxy, oxo, halo, haloalkyl, hydroxy, hydroxyalkyl, amino, alkylamino, dialkylamino, nitro, and cyano. Additionally, the suitable indicated groups can include, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —C(=O)R, —C(=O)X, —C(O)OR, where each X is independently a halogen ("halo"): F, Cl, Br, or I; and each R is independently H or alkyl. As would be readily understood by one skilled in the art, when a substituent is oxo (=O), or the like, then two hydrogen atoms on the substituted atom are replaced.

Synthesis

In some embodiments, the present invention provides a method for synthesizing trehalose analogues comprising contacting a glucose analogue with a trehalose synthase, a magnesium salt, and a monosaccharide donor. In some embodiments, the present invention provides trehalose analogues quickly, e.g. in about 1 hour, in a high yield, e.g. up to 99%, in a single step from readily available glucose analogues.

Scheme 1. Synthesis of trehalose from glucose (glc) and UDP-glucose (UDP-glc) by TreT from Thermoproteus tenax.

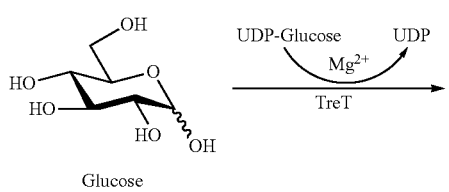

Glucose

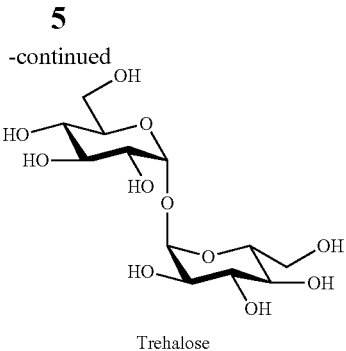

Trehalose

In some embodiments, the monosaccharide donor is a nucleotide diphosphate monosaccharide, such as UDP-glucose, ADP-glucose, GDP-glucose, UDP-galactose, or GDP-mannose. For example, the nucleotide diphosphate may be uridine diphosphate (UDP), guanosine diphosphate (GDP), or adenosine diphosphate (ADP) and the monosaccharide may be glucose, galactose, allose, or mannose. In some embodiments, the monosaccharide may be labeled, e.g. with a radioactive or other isotope, such as $^{11}C$, $^{13}C$, $^{14}C$, $^{2}H$, $^{3}H$, $^{15}O$, $^{18}O$, $^{13}N$, $^{15}N$, $^{35}S$, $^{18}F$ and $^{125}I$. In other embodiments, the monosaccharide donor is glucosyl fluoride.

The magnesium salt is suitably magnesium chloride. The reaction may further comprise a buffer, such as HEPES, Tris, or other common biological buffers. In some embodiments, the reaction is performed at a pH of about 7 to about 7.5.

In some embodiments, the methods of the present invention may provide a yield of at least about 80%, at least about 85%, at least about 90%, at least about 95%, at least about 97%, at least about 98%, or at least about 99%. In some embodiments, the methods of the present invention may be performed in less than about 1 hour, less than about 2 hours, less than about 3 hours, less than about 6 hours, less than about 12 hours, or less than about 24 hours.

In some embodiments, the trehalose synthase is thermostable. In some embodiments, the trehalose synthase is unidirectional, meaning that it does not degrade trehalose. In some embodiments, the trehalose synthase is from *Thermoproteus tenax*. Suitable trehalose synthases include, but are not limited to, those in *Thermoccus litoralis, Pyrococcus horikoshii, Thermoproteus tenax, Rubrobacter xylanphilus, Pimelobacter* sp., *Thermus aquaticus, Sulfolobus* sp. The trehalose synthase may be isolated and purified from *E. coli* by techniques known to one of ordinary skill in the art.

In some embodiments, the glucose analogue is a monosaccharide. The analogue may be a natural sugar, such as mannose, galactose, or allose, or a non-natural sugar, such as a modified glucose, modified mannose, modified galactose, or a modified allose. In some embodiments, the glucose analogue is modified at the 2-, 3-, 4- and/or 6-positions. In some embodiments, the glucose analogue may contain stereochemical modifications. Certain glucose analogues suitable for use in the present invention contain both substituent modifications and stereochemical modifications. In some embodiments, the glucose analogue contains one or more of the following modifications: a stereochemical modification; a halo substituent, such as fluoro or chloro; a deoxy modification; an azido substituent; a hydroxyl substituent; a ring sulfur; an isotope.

In some embodiments, the glucose analogue may contain one or more isotopes, such as, but not limited to, $^{11}C$, $^{13}C$, $^{14}C$, $^{2}H$, $^{3}H$, $^{15}O$, $^{18}O$, $^{13}N$, $^{15}N$, $^{35}S$, $^{18}F$ and $^{125}I$. In some embodiments, one or more of the isotopes may be a radioactive isotope. In some embodiments, an isotope may be located at any position in the glucose analogue. For example, the ring may contain an isotope. In some embodiments, an isotope may be found in one or more of $R^1$, $R^2$, $R^3$ and $R^4$. In some embodiments, an isotope may be located in the ring and in one or more of $R^1$, $R^2$, $R^3$ and $R^4$.

In some embodiments, the glucose analog may be further substituted by a detectable moiety that is detectable upon exposure to an external stimulus. In some embodiments, the detectable moiety may be a reactive chemical handle (e.g. a biorthoganol tag such as azido, alkynyl, or cylcopropenyl), a fluorophore, a luminescent moiety (e.g. a chemiluminescent moiety, a thermoluminescent moiety, or an electroluminescent moiety), or a phosphorescent moiety. Suitable fluorophores include, but are not limited to, fluoresceins, xanthenes, cyanines, naphthalenes, coumarins, oxadiazoles, pyrenes, oxazines, acridines, arylmethines, Alexa Fluors and tetrapyrroles. In some embodiments, the detectable moiety is attached to the glucose analogue through a reactive chemical moiety such as azido, alkynyl or cyclopropenyl.

The glucose analogue may suitably be a compound of Formula (I):

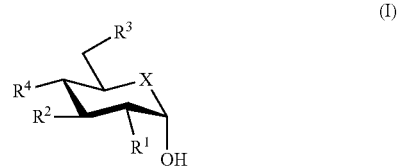

wherein
  X is O, S, Se, PH, P(O)H, or P(O)OH;
  $R^1$, $R^2$ and $R^3$ are independently selected from H, halo, —OR, —NR$_2$, —NR$_3^+$, —NHCOR, —SR, —SCOR, —OPO$_3^{2-}$, —SeR, —SeCOR, —N$_3$, —CN, —NC, C$_{1-6}$ alkyl, C$_{2-6}$ alkenyl, or C$_{2-6}$ alkynyl;
  $R^4$ is OH, —NHR, —SH, or —SeH; and
  each R is independently selected from H, C$_{1-6}$ alkyl, C$_{2-6}$ alkenyl or C$_{2-6}$ alkynyl.

The glucose analogue may suitably be a compound of Formula (II):

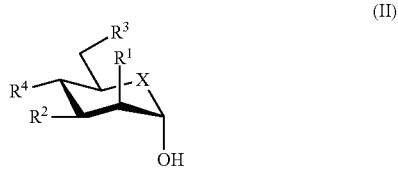

wherein
  X is O, S, Se, PH, P(O)H, or P(O)OH;
  $R^1$, $R^2$ and $R^3$ are independently selected from H, halo, —OR, —NR$_2$, —NR$_3^+$, —NHCOR, —SR, —SCOR, —OPO$_3^{2-}$, —SeR, —SeCOR, —N$_3$, —CN, —NC, C$_{1-6}$ alkyl, C$_{2-6}$ alkenyl, or C$_{2-6}$ alkynyl;
  $R^4$ is OH, —NHR, —SH, or —SeH; and
  each R is independently selected from H, C$_{1-6}$ alkyl, C$_{2-6}$ alkenyl or C$_{2-6}$ alkynyl.

As described herein, all glucose and trehalose analogues include all possible isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Exemplary substrates and their products are shown in FIGS. 1A-D.

Use of Trehalose Analogues

Figure 4:
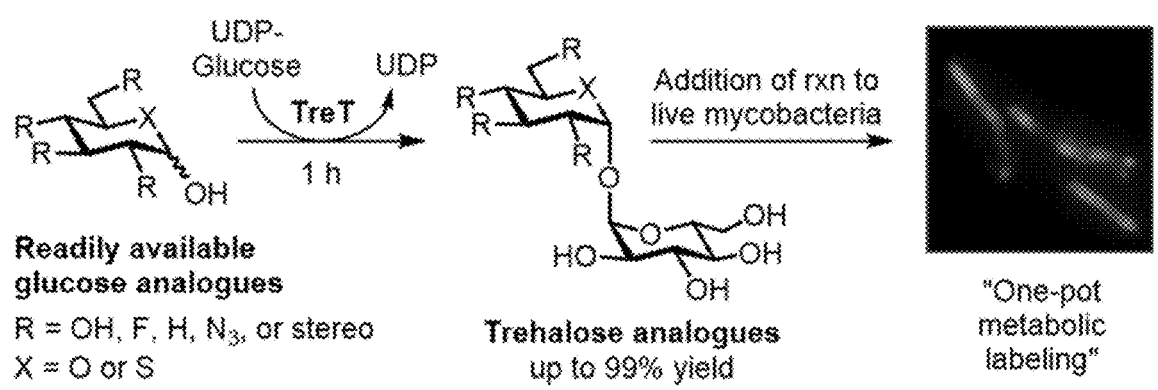
FIG. 4 shows the one-pot metabolic labeling.

The present invention also provides a simple method for the synthesis and use of chemical probes to detect live mycobacteria, e.g., *Mycobacterium tuberculosis*, and possibly other trehalose-containing organisms/pathogens. In some embodiments, this method is performed without purification of the enzymatic reaction. This is referred to as "one-pot metabolic labeling." One-pot metabolic labeling capitalizes on the biocompatible nature of enzymatic reactions. After performing the enzymatic reaction as described above, the reaction mixture containing the trehalose analogue product can be directly added to a sample containing live mycobacteria (or possibly other trehalose-containing organisms/pathogens) with no or minimal processing or purification of the enzymatic reaction (as shown in Scheme 2). The mycobacteria (or possibly other trehalose-containing organisms/pathogens) take up the trehalose analogue from the aqueous enzymatic reaction mixture, leading to labeling of the cell. If the trehalose analogue is detectable (e.g., $^{14}C$-, $^{18}F$-, $^{3}H$, or $N_3$-labeled or labeled with a reactive chemical handle, a fluorophore, a luminescent moiety or a phosphorescent moiety), then mycobacteria (or possibly other trehalose-containing organisms/pathogens) are readily detected using traditional analytical methods known to one skilled in the art, such as positron emission topography (PET), autoradiographic analysis, scintillation detection, magnetic resonance imaging (MRI), nuclear magnetic resonance (NMR), x-ray photography, computed tomography (CT), single photon emission computed tomography (SPECT) and fluorescence microscopy. In some embodiments, one-pot metabolic labeling provides trehalose analogue synthesis, metabolic labeling, and imaging of mycobacteria in about 1 hour, or about 2 hours or about 3 hours or about 5 hours or about 10 hours. This one-pot approach is useful for rapidly synthesizing and administering trehalose analogues to mycobacteria (or possibly other trehalose-containing organisms/pathogens). See FIG. 4.

The present invention also provides a method of determining the presence of mycobacteria species in a subject or sample. In some embodiments, the method comprises adding a labeled trehalose analogue to an organism or sample. The presence of mycobacteria is then determined by detecting the labeled trehalose analogue. Without wishing to be bound by theory, the labeled trehalose analogue accumulates in mycobacteria via a trehalose-specific transport protein, such as SugABC-LpqY. In some embodiments, the trehalose analogue is labeled with an isotope, such as $^{18}F$. In some embodiments, the trehalose analog is labeled with a detectable moiety such as a fluorophore, a luminescent moiety or a phosphorescent moiety.

The methods of the present invention are useful in cells grown in culture medium, i.e., in vitro, or in cells within animals, e.g., living animals, i.e., in vivo. For research purposes, for measurements in cells in vivo, a trehalose analogue as described herein is administered, e.g., injected into the animal or added to an aqueous solution, e.g., water, or food consumed by the animal, to the animal. The methods of the present invention may be used in intact cells or in isolated organelles.

Cells may be mammalian cells, including but not limited to human, simian, murine, canine, bovine, equine, feline, ovine, caprine or swine cells, or prokaryotic cells, or cells from two or more different organisms, or cell lysates or supernatants thereof. In certain aspects, the cell may be in an animal, or physiological fluid, e.g., blood, plasma, urine, mucous secretions or the like.

In some embodiments, the sample is a biological sample such as tissue, cells, bodily fluid, sputum, cerebrospinal fluid, pericardial fluid, synovial fluid, ascitic fluid, blood, bone marrow, urine, or feces.

Trehalose Analogues

The present application also provides various trehalose analogues. In some embodiments, the trehalose analogue is a compound according to Formula (III) or Formula (IV):

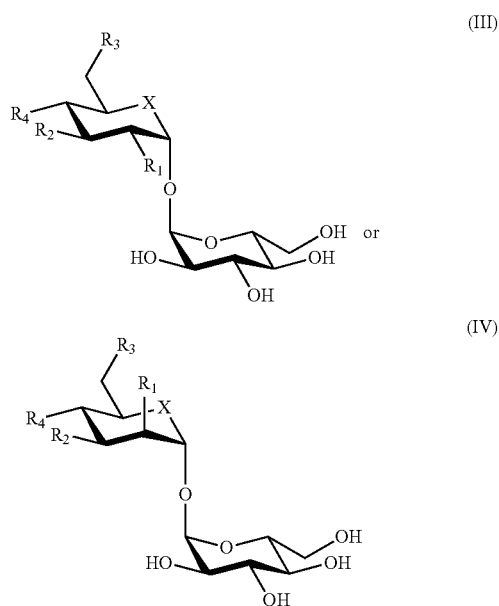

wherein

X is O, S, Se, PH, P(O)H, or P(O)OH;

$R^1$, $R^2$ and $R^3$ are independently selected from H, halo, —OR, —$NR_2$, —$NR_3^+$, —NHCOR, —SR, —SCOR, —$OPO_3^{2-}$, —SeR, —SeCOR, —$N_3$, —CN, —NC, $C_{1-6}$ alkyl, $C_{2-6}$ alkenyl, or $C_{2-6}$ alkynyl;

$R^4$ is OH, —NHR, —SH, or —SeH; and each R is independently selected from H, $C_{1-6}$ alkyl, $C_{2-6}$ alkenyl or $C_{2-6}$ alkynyl;

with the proviso that the analogue is not trehalose.

Trehalose analogues contemplated by the present invention include, but are not limited to:

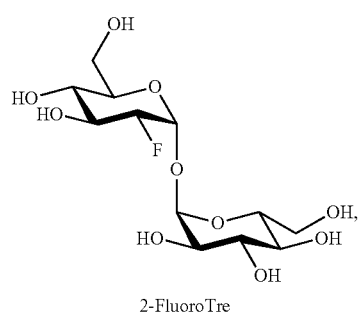

2-FluoroTre

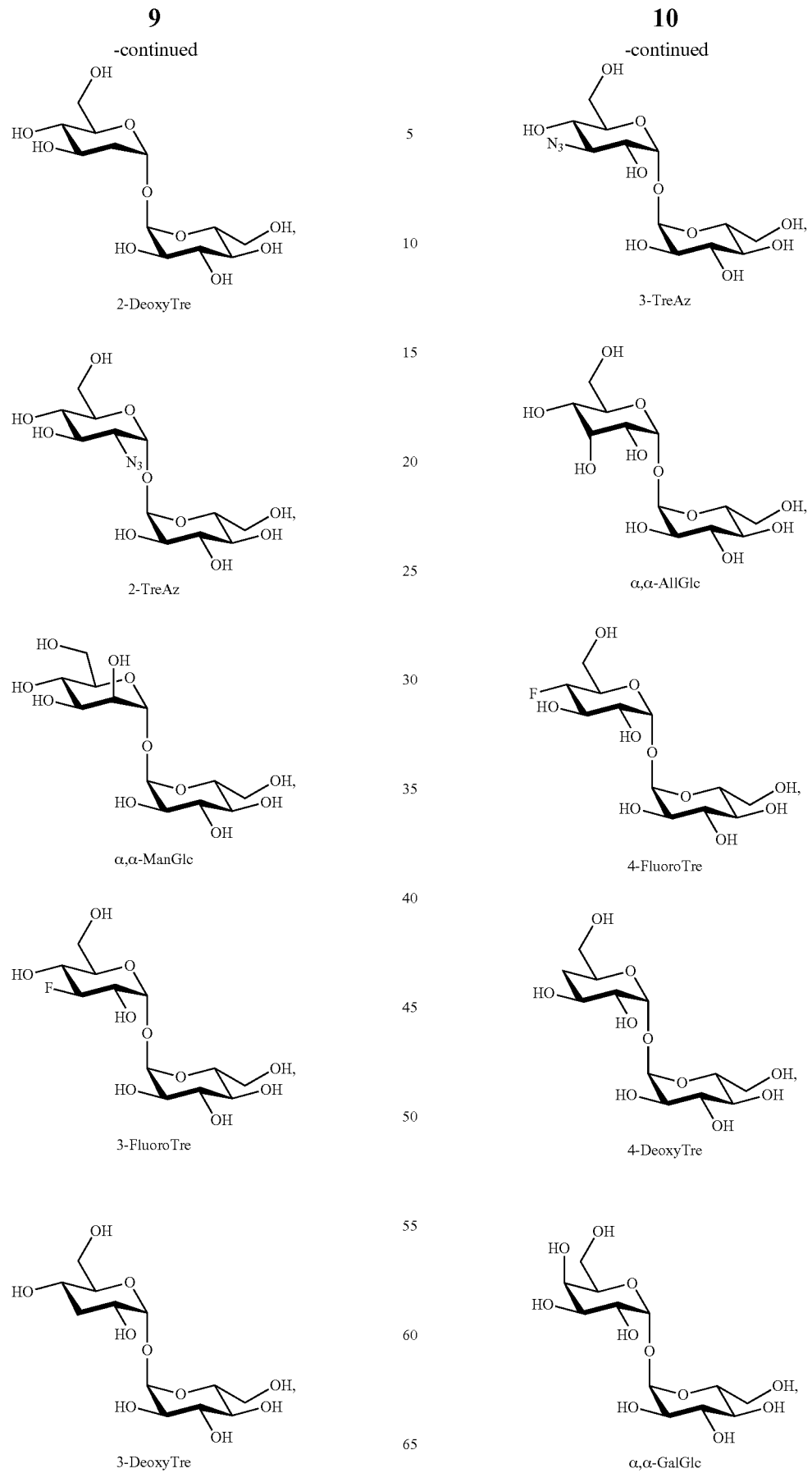

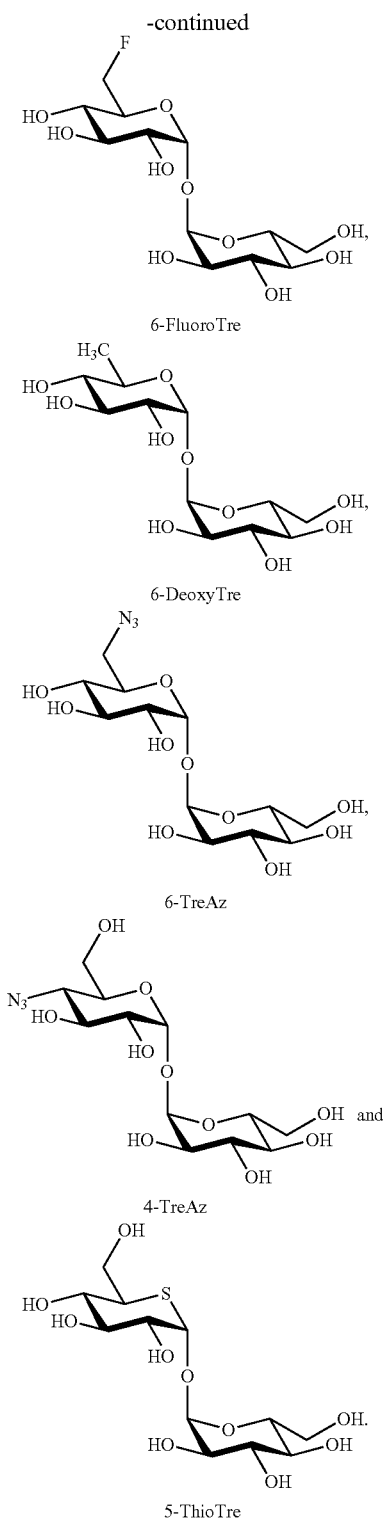

6-FluoroTre

6-DeoxyTre

6-TreAz

4-TreAz and

5-ThioTre

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

EXAMPLES

Example 1: Materials and Methods for Examples 2 and 3

General Experimental Section: Materials and reagents were obtained from commercial sources without further purification. Most glucose analogues were obtained from Sigma-Aldrich (2-GlcAz, 2-DeoxyGlc, 6-GlcAz), Carbo-Synth (2-FluoroGlc, 3-DeoxyGlc, 3-FluoroGlc, 4-DeoxyGlc, 4-FluoroGlc, 6-DeoxyGlc, 6-FluoroGlc), or Santa Cruz Biotechnology (5-ThioGlc). 3-GlcAz and 4-GlcAz were chemically synthesized according to literature-reported procedures. Chromatographic analysis of reactions was performed using a Perkin Elmer Series 200 high-performance liquid chromatography (HPLC) system equipped with a Perkin Elmer Series 200 refractive index detector. High-resolution electrospray ionization (HR ESI) mass spectra were obtained in negative mode using a Waters LCT Premier XE using raffinose as the lock mass. $^1$H NMR and $^{13}$C NMR spectra were recorded on a Varian Inova 500 MHz NMR. Analytical TLC was performed on glass-backed silica gel 60 Å plates (thickness 250 μm) from Dynamic Adsorbents and detected by charring with 5% $H_2SO_4$ in EtOH. Column chromatography was performed using flash-grade silica gel 32-63 μm (230-400 mesh) from Dynamic Adsorbents.

Cloning, Expression, and Purification of TreT:

The treT gene encoding trehalose synthase from *Thermoproteus tenax* was codon-optimized for *E. coli* and synthesized by Life Technologies. The optimized treT sequence was cloned into the pBAD/His A vector using restriction sites KpnI and SacI on the N-terminus and C-terminus, respectively, and verified by sequencing. The resultant pBAD-HisA TreT plasmid encodes an N-terminal 6×histidine tag on the protein. The plasmid was transformed into Top10 chemically competent *E. coli* and plated on LB agar containing 100 m/mL ampicillin.

To express the TreT protein, a 3 mL LB/ampicillin culture was inoculated with a single colony and grown overnight in a shaking incubator at 37° C. The following day, this 3 mL culture was used to inoculate a 600 mL culture of Terrific Broth with 100 m/mL ampicillin. Once the inoculated culture reached mid-log phase, it was induced with arabinose (final concentration of arabinose=1 mM) and grown in a shaking incubator overnight at 37° C.

Cells were then spun at 4000×g and the pellets resuspended in 20 mL of Equilibration/Lysis/Wash buffer (300 mM NaCl, 50 mM $NaH_2PO_4$, 20 mM imidazole). Resuspended pellets were sonicated using a Fisher Scientific Sonifier (3×45 s, 75% amplitude). Sonicated cells were spun at 15,000×g for 20 minutes to clarify the lysate. Next, lysates were loaded on a 5 mL Bio-Rad Bio-scale Mini Profinity immobilized metal affinity chromatography (IMAC) cartridge at 5 mL/minute and washed until the $A_{280}$ reached background levels. TreT protein was eluted using a gradient containing high imidazole buffer (300 mM NaCl, 50 mM $NaH_2PO_4$, 250 mM imidazole). Protein samples were concentrated in an Amicon Ultra 15 mL concentrator with a 10,000 molecular weight cutoff. Elution buffer was exchanged for 300 mM NaCl, 50 mM HEPES, pH 7. Protein samples were analyzed by SDS-PAGE to verify protein purity and concentration was assessed using UV-Vis spectroscopy.

General Method for Enzymatic Reactions:

Concentrated (10×) stock solutions of the reaction reagents in 50 mM HEPES buffer (pH 7.4) included glucose analogues (100 mM), UDP-Glc (400 mM), and $MgCl_2$ (200 mM). Microscale reactions (50 µL) were performed by addition of 5 µL of each reagent and an appropriate volume of HEPES buffer, followed by addition of TreT to a final concentration of 9.8 µM to initiate the reaction. Reactions were incubated at 70° C. with gentle shaking for 1 h, after which an equal volume of ice-cold HPLC-grade acetone (50 µL) was added to quench the reaction. After cooling at −20° C. for 1 h, reactions were centrifuged at 11,900 rpm for 20 min, and the supernatant was collected and directly analyzed by HPLC (column: Imtakt UK-Amino 250×46 mm at 50° C.; mobile phase: isocratic elution with pre-mixed 80% acetonitrile in water; flow rate: 0.4 mL/min; detection: refractive index). Yields were calculated by comparing relative peak areas of substrates and products.

$^1$H NMR, $^{13}$C NMR, and HR ESI MS Data for Semi-Preparative Reaction Products:

Semi-preparative reactions were performed exactly as described above only in larger final volumes (1.5-2.0 mL). After incubation for 1 h at 70° C., reactions were quenched by addition of an equal volume of cold acetone, cooled at −20° C. for 1 h, and centrifuged at 11,900 rpm for 20 min. The supernatant was collected and concentrated in vacuum, and the resulting residue was resuspended in $CH_2Cl_2$/$CH_3OH$ (1:1) and passed through a silica plug using $CH_2Cl_2$/$CH_3OH$ (1:1) as the eluent. If necessary, further purification was accomplished by silica gel column chromatography using an elution solvent of $CH_2Cl_2$/$CH_3OH$ (2:1 or 2.5:1). After concentration, the purified products were redissolved in water, filtered (0.2 µm), and concentrated to give white solids.

2-Deoxy-2-fluoro-α,α-D-trehalose (2-FluoroTre)

From 3.6 mg 2-FluoroGlc, obtained 6.6 mg 2-FluoroTre (97%). $^1$H NMR (500 MHz, $D_2O$): δ 5.41 (d, J=3.5 Hz, 1H), 5.19 (d, J=3.5 Hz, 1H), 4.48 (ddd, $J_{H,H}$=3.5, 9.5 Hz, $J_{H,F}$=49 Hz, 1H), 4.10 (dt, $J_{H,H}$=9.5 Hz, $J_{H,F}$=13.5 Hz, 1H), 3.88-3.72 (m, 7H), 3.63 (dd, J=3.5, 10 Hz, 1H), 3.49 (t, J=9.0 Hz, 1H), 3.43 (t, J=10 Hz, 1H). $^{13}$C NMR (125 MHz, $D_2O$): δ 93.97, 91.15 (d, $J_{C,F}$=22 Hz), 89.44 (d, $J_{C,F}$=188 Hz), 72.54, 72.16, 71.05 (d, $J_{C,F}$=17 Hz), 70.89, 69.51, 69.02, 68.96, 60.43, 60.22. HR ESI MS negative mode: calcd. for $C_{12}H_{21}ClFO_{10}$ [M+Cl]$^-$ m/z, 379.0807; found, 379.0800.

2-Deoxy-α,α-D-trehalose (2-DeoxyTre)

From 3.3 mg of 2-DeoxyGlc, obtained 6.2 mg 2-DeoxyTre (94%). $^1$H NMR (500 MHz, $D_2O$): δ 5.28 (d, J=3.0 Hz, 1H), 5.13 (d, J=3.5 Hz, 1H), 4.03 (m, 1H), 3.86-3.72 (m, 6H), 3.67 (m, 1H), 3.59 (dd, J=3.5, 9.5 Hz, 1H), 3.42 (t, J=9.0 Hz, 1H), 3.38 (t, J=9.0 Hz, 1H), 2.20 (dd, J=5.0, 13 Hz, 1H), 1.75 (dt, J=3.5, 13 Hz). $^{13}$C NMR (125 MHz, $D_2O$): δ 93.19, 92.30, 72.64, 72.61, 72.12, 70.90, 69.59, 67.88, 60.57, 60.43, 36.27. HR ESI MS negative mode: calcd. for $C_{12}H_{22}ClO_{10}$ [M+Cl]$^-$ m/z, 361.0902; found, 361.0884.

3-Deoxy-3-fluoro-α,α-D-trehalose (3-FluoroTre)

From 3.6 mg of 3-FluoroGlc, obtained 6.5 mg 3-FluoroTre (96%). $^1$H NMR (500 MHz, $D_2O$): δ 5.23 (t, J=3.5 Hz, 1H), 5.17 (d, J=4.0 Hz, 1H), 4.74 (dt, $J_{H,H}$=9.5 Hz, $J_{H,F}$=55 Hz, 1H), 3.92 (m, 1H), 3.87-3.73 (m, 7H), 3.63 (dd, J=3.5, 9.5 Hz, 1H), 3.43 (t, J=9.5 Hz, 1H). $^{13}$C NMR (125 MHz, $D_2O$): δ 94.27 (d, $J_{C,F}$=178 Hz), 93.43 (d, $J_{C,F}$=10.5 Hz), 93.35, 72.41, 72.14, 71.59 (d, $J_{C,F}$=6.6 Hz), 70.88, 69.53, 69.45 (d, $J_{C,F}$=20 Hz), 67.80 (d, $J_{C,F}$=17 Hz), 60.40, 60.00. HR ESI MS negative mode: calcd. for $C_{12}H_{21}ClFO_{10}$ [M+Cl]$^-$ m/z, 379.0807; found, 379.0794.

6-Azido-6-Deoxy-α,α-D-trehalose (6-TreAz)

From 4.1 mg of 6-GlcAz, obtained 6.7 mg 6-TreAz (92%). $^1$H NMR (500 MHz, $D_2O$): δ 5.05 (d, J=4.5 Hz, 1H), 5.04 (d, J=4.0 Hz, 1H), 3.82 (ddd, J=2.5, 6.0, 10.5 Hz, 1H), 3.72-3.67 (m, 4H), 3.61 (dd, J=5.0, 12 Hz, 1H), 3.55-3.49 (m, 3H), 3.42 (dd, J=5.5, 13.5 Hz, 1H), 3.31 (t, J=9.5 Hz, 1H), 3.30 (t, J=9.0 Hz, 1H). $^{13}$C NMR (125 MHz, $D_2O$): δ 93.53, 93.33, 72.43, 72.23, 72.12, 70.91, 70.89, 70.86, 70.38, 69.57, 60.40, 50.78. HR ESI MS negative mode: calcd. for $C_{12}H_{21}ClN_3O_{10}$ [M+Cl]$^-$ m/z, 402.0915; found, 402.0922.

5-Deoxy-5-Thio-α,α-D-trehalose (5-ThioTre)

From 3.9 mg of 5-ThioGlc, obtained 6.5 mg 5-ThioTre (92%). $^1$H NMR (500 MHz, $D_2O$): δ 5.41 (d, J=4.0 Hz, 1H), 4.98 (d, J=3.5 Hz, 1H), 3.93 (dd, J=3.0, 10 Hz, 1H), 3.89-3.77 (m, 6H), 3.75 (dd, J=5.0, 11 Hz, 1H), 3.67-3.63 (m, 2H), 3.44 (t, J=9.5 Hz, 1H), 3.13 (m, 1H). $^{13}$C NMR (125 MHz, $D_2O$): δ 93.48, 76.99, 74.76, 73.62, 73.53, 72.71, 72.24, 70.92, 69.63, 60.43, 59.90, 42.87. HR ESI MS negative mode: calcd. for $C_{12}H_{22}ClO_{10}S$ [M+Cl]$^-$ m/z, 393.0622; found, 393.0606.

One-Pot Metabolic Labeling and Imaging of *M. smegmatis*:

Cultures of *M. smegmatis* wild type, ΔsugC mutant, or ΔsugC::sugC complement were generated by inoculating a single colony from a freshly streaked agar plate (with appropriate antibiotic, if needed) into 3 mL Middlebrook 7H9 liquid medium supplemented with ADC (albumin, dextrose, and catalase), 0.5% glycerol, and 0.05% Tween-80 in a culture tube. Starter cultures were incubated at 37° C. with shaking until reaching log phase. Meanwhile, using the procedure described above, a 50 µL TreT reaction employing 6-GlcAz (10 mM) as the substrate was carried out to synthesize 6-TreAz (+TreT sample). A control reaction lacking TreT was run in parallel (−TreT control). After incubation at 70° C. for 1 h, the reactions were stopped by placing on ice. Given the observed quantitative conversion for this reaction (FIG. 1B, Entry 16), a 6-TreAz concentration of 10 mM was assumed in the +TreT sample. For the −TreT control, a 6-GlcAz concentration of 10 mM was assumed. The aqueous reaction mixtures were directly diluted into *M. smegmatis* wild type, ΔsugC mutant, or ΔsugC::sugC complement growing in 7H9 liquid medium to a final azido sugar concentration of 25 µM and a culture density of $OD_{600}$=0.15. Control experiments in which bacterial strains were cultured only in 7H9 liquid medium were run in parallel. Bacteria were incubated at 37° C. for 4 h (final densities of all cultures were $OD_{600}$=0.60-0.64), after which cells were pelleted (5000 rpm for 5 min) and washed three times with phosphate-buffered saline supplemented with 0.5% BSA (PBS-B), then fixed by treatment with 4% paraformaldehyde in PBS for 15 min. Fixed cells were pelleted and washed once with PBS-B, then reacted with alkyne-modified carboxyrhodamine 110 fluorophore (Click Chemistry Tools) via Cu-catalyzed azide-alkyne cycloaddition (CuAAC) according to Breidenbach et al., Proc. Natl. Acad. Sci. U.S.A. (2010) 108, 3141 and Swarts et al., J. Am.

Chem. Soc. (2012) 134, 16123, the entire contents of both of which are incorporated herein by reference. Following CuAAC, cells were pelleted and washed three times with PBS-B. 10 uL of bacteria resuspended in PBS were spotted onto a microscope slide, lightly spread into a thin layer using the edge of a coverslip, and allowed to air dry in the dark. Fluoromount-G mounting medium (SouthernBiotech) was applied, then cover slips were placed over the sample and immobilized with adhesive. Microscopy was carried out using an EVOS FL (Life Technologies) inverted microscope equipped with a 100×1.4 numerical aperture Plan-Apochromat oil immersion lens. Fluorescence imaging was performed using a GFP LED light cube (maximum excitation/emission=470/510 nm). Images were captured with a Sony ICX445 CCD camera and processed using the FIJI distribution of Image." Image acquisition and processing were performed identically for all samples.

Genetic Complementation of the M. smegmatis ΔsugC Mutant Strain:

The sugC gene (MSMEG_5058) was amplified from genomic DNA of M. smegmatis mc²155 by PCR using the oligonucleotide pair

```
                                        (SEQ ID NO: 1)
5'-TTTTTTTAATTAAATGGCCGAAATTGTGTTGGATCG-3'
and (SEQ ID NO: 2)
5'-TTTTTAAGCTTCACCCGGCGTCCGGCCCCGCCG-3'
``` and cloned using the restriction enzymes PacI and HindIII (underlined) into the single-copy integrative plasmid pMV361(Apra)-PacI, a derivative of pMV361(Kan) containing an apramycin resistance gene and a unique PacI restriction site. The resulting plasmid pMV361(Apra)::MSMEG_5058 was then transformed by electroporation into the M. smegmatis ΔsugC mutant yielding the complemented mutant strain M, smegmatis ΔsugC::sugC with stable chromosomal integration of the plasmid into the mycobacteriophage L5 attB site, providing constitutive sugC gene expression from the HSP60 promoter. Solid medium containing 50 mg/L hygromycin and 10 mg/L apramycin was used for selection.

Example 2: Trehalose Analogue Synthesis

Studies were performed to synthesize trehalose analogues using trehalose synthase TreT from the hyperthermophile Thermoproteus tenax, for example, as shown in Scheme 1 below. Specifically, scheme 1 shows the synthesis of trehalose from Glc and UDP-Glc by TreT from T. tenax.

Scheme 1

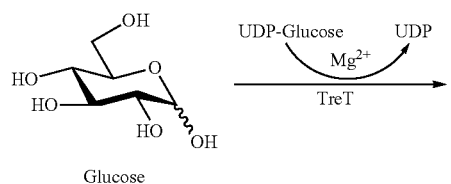

Glucose

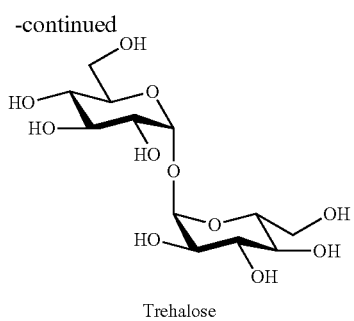

Trehalose

TreT was expressed and purified from E. coli and screened for reactivity using a panel of monofunctionalized Glc analogues (FIGS. 1A, 1B, and 1C). The Glc analogues that were tested contained fluoro-, deoxy-, azido-, and stereochemical modifications occurring at all positions of the sugar ring, which afforded a systematic evaluation of TreT substrate specificity. Reactions were performed in 50 mM HEPES buffer (pH 7.4) containing 10 mM Glc analogue, 40 mM UDP-Glc, 20 mM $MgCl_2$, and 9.8 μM TreT (reaction volume 50 μL). The reactions were incubated at 70° C. with gentle shaking for 1 h, quenched by addition of cold acetone, and analyzed by HPLC and high-resolution ESI mass spectrometry as described above in Example 1.

The Glc analogues which were evaluated were well-tolerated by TreT (FIGS. 1A, 1B, and 1C). In most cases, the corresponding trehalose analogue products were generated in excellent yield after only 1 h, which highlighted the efficiency, rapidity, and generality of the method. Fluoro-, deoxy-, azido-, and stereochemical modifications of the Glc 2-, 3-, and 6-positions were generally accepted, except for azido substitution at the 2-position and inversion of the 3-OH group. Glc analogues bearing 4-position alterations were poor substrates (N.D.—26% yield), indicating a strict specificity at this position. Finally, 5-thio-D-glucose, the sole 5-position-modified Glc analogue that was tested, was converted to 5-thio-trehalose in quantitative yield.

Selected reactions were run on a semi-preparative scale (5-10 mg) to evaluate the scalability of the method and to confirm product structure by NMR spectroscopy. Semi-preparative reactions were performed as described above and the products were readily purified by silica gel chromatography. Consistent with the small-scale results, 2-Fluoro-Tre, 2-DeoxyTre, 3-FluoroTre, 6-TreAz, and 5-ThioTre were obtained in isolated yields of 92-97%. $^1$H and $^{13}$C NMR analysis established the product structures, including the assignment of 1,1-α,α-stereochemistry for newly formed glycosidic bonds (see Example 1).

Example 3: Single-Day Probe Synthesis, Metabolic Labeling, and Imaging

Figure 2A:
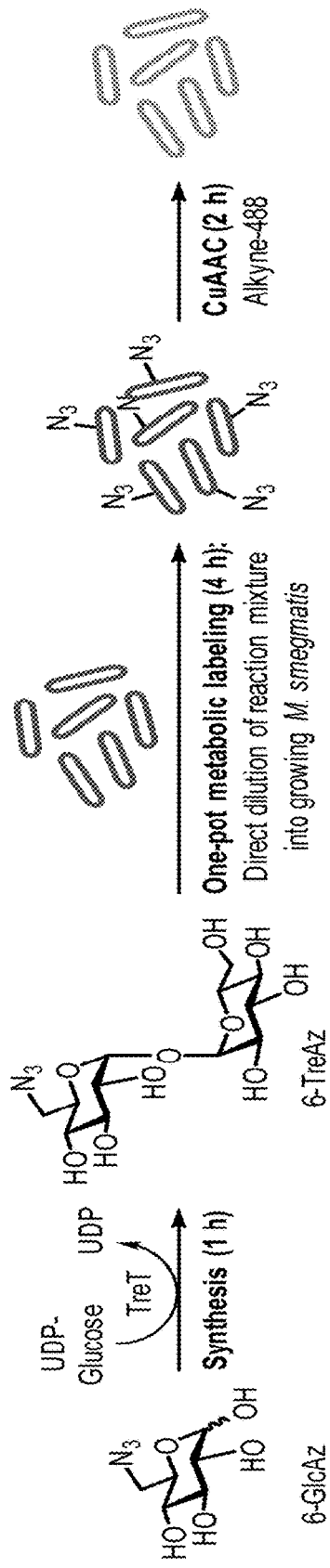
FIG. 2A and FIG. 2B.

To evaluate the applicability of the method described in Example 2 to imaging mycobacteria, a one-day experiment was performed that encompassed probe synthesis, metabolic labeling, and imaging of M. smegmatis, which is an avirulent model organism frequently used in tuberculosis (TB) research (FIG. 2A).

First, TreT was used to convert commercially available 6-azido-6-deoxy-D-glucose (6-GlcAz) to 6-TreAz (FIG. 1B, Entry 16), an established chemical reporter for metabolic labeling of mycobacterial glycolipids. Next, the biocompatibility of enzymatic reactions was utilized by directly diluting the aqueous TreT reaction mixture into live *M. smegmatis* cell suspension, which is referred to herein as "one-pot metabolic labeling." After incubation for 4 h, 6-TreAz-labeled mycobacteria were washed, fixed, and reacted with an azide-reactive fluorophore, alkyne-488, via Cu-catalyzed azide-alkyne cycloaddition (CuAAC).

Figure 2B:
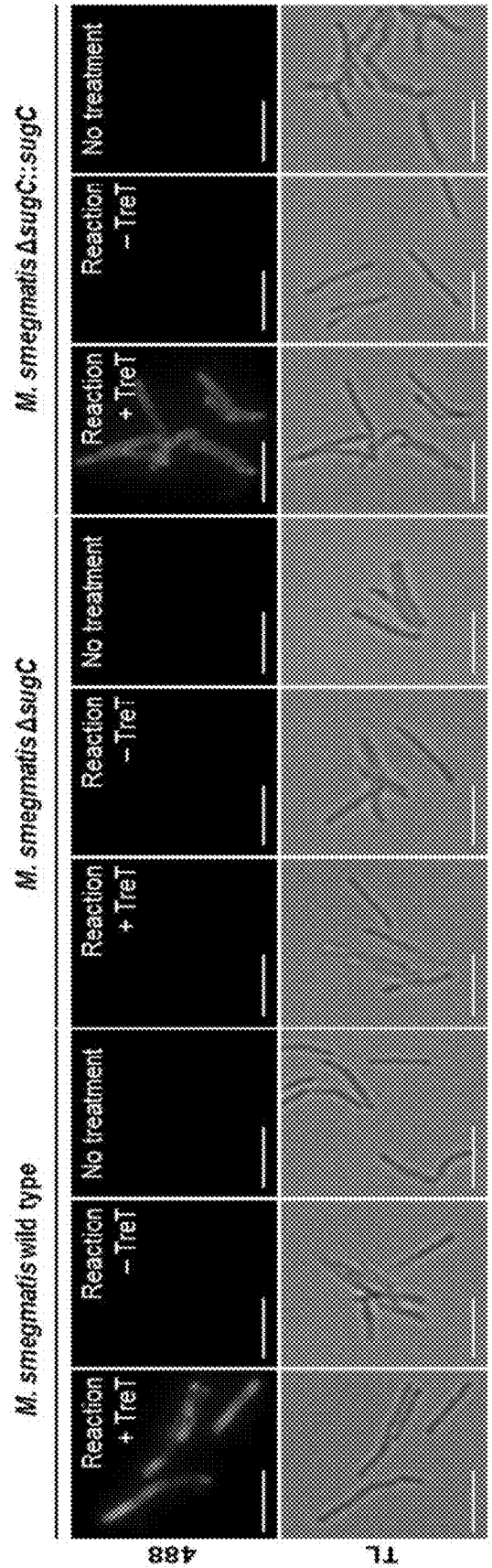

As shown in FIG. 2B, fluorescence microscopy revealed strong labeling of wild-type *M. smegmatis* that was treated with a reaction mixture containing 6-TreAz (+TreT). No fluorescence was observed when bacteria were treated with a reaction mixture lacking TreT (−TreT), which consisted only of unreacted substrates.

The same experiments were performed in *M. smegmatis* ΔsugC, a mutant missing the trehalose transporter required for 6-TreAz uptake and labeling, as well as its complement, *M. smegmatis* ΔsugC::sugC. Fluorescence was abolished in the ΔsugC mutant and restored in the complement, confirming that 6-TreAz labeling proceeded via the trehalose transporter pathway.

Additionally, direct treatment of *M. smegmatis* with TreT reaction mixture had no effect on bacterial growth or appearance. This operationally simple experiment provided a model for rapidly preparing and administering trehalose-based chemical probes. By contrast, traditional methods for synthesizing and purifying these compounds can require several weeks of work by a trained chemist in a well-equipped synthesis laboratory.

Example 4: Uptake of Fluoro Trehalose by the Trehalose Transporter in Mycobacteria Cultures of *M. smegmatis* wild type, ΔsugC mutant, or ΔsugC::sugC complement were generated by inoculating a single colony from a freshly streaked agar plate (with appropriate antibiotic, if needed) into 3 mL Middlebrook 7H9 liquid medium supplemented with ADC (albumin, dextrose, and catalase), 0.5% glycerol, and 0.05% Tween-80 in a culture tube. Starter cultures were incubated at 37° C. with shaking until reaching log phase. Cells were then cultured at 37° C. in the presence or absence of 2-, 3-, 4-, or 6-fluoro trehalose (100 μM) in 7H9 liquid medium for 1 h, then centrifuged and washed (5000 rpm for 5 min) three times in ultrapure water. The washed cells were resuspended in ultrapure water and boiled for 4 h, then centrifuged. The supernatant was collected and dried on a speedvac to yield water-soluble cytosolic metabolites (e.g., trehalose and fluoro trehaloses, if present), which were subsequently trimethylsilyl (TMS)-derivatized using N-Methyl-N-(trimethylsilyl) trifluoroacetamide (MSTFA) in pyridine and analyzed by gas chromatography-mass spectrometry (GC-MS).

Figure 3A:
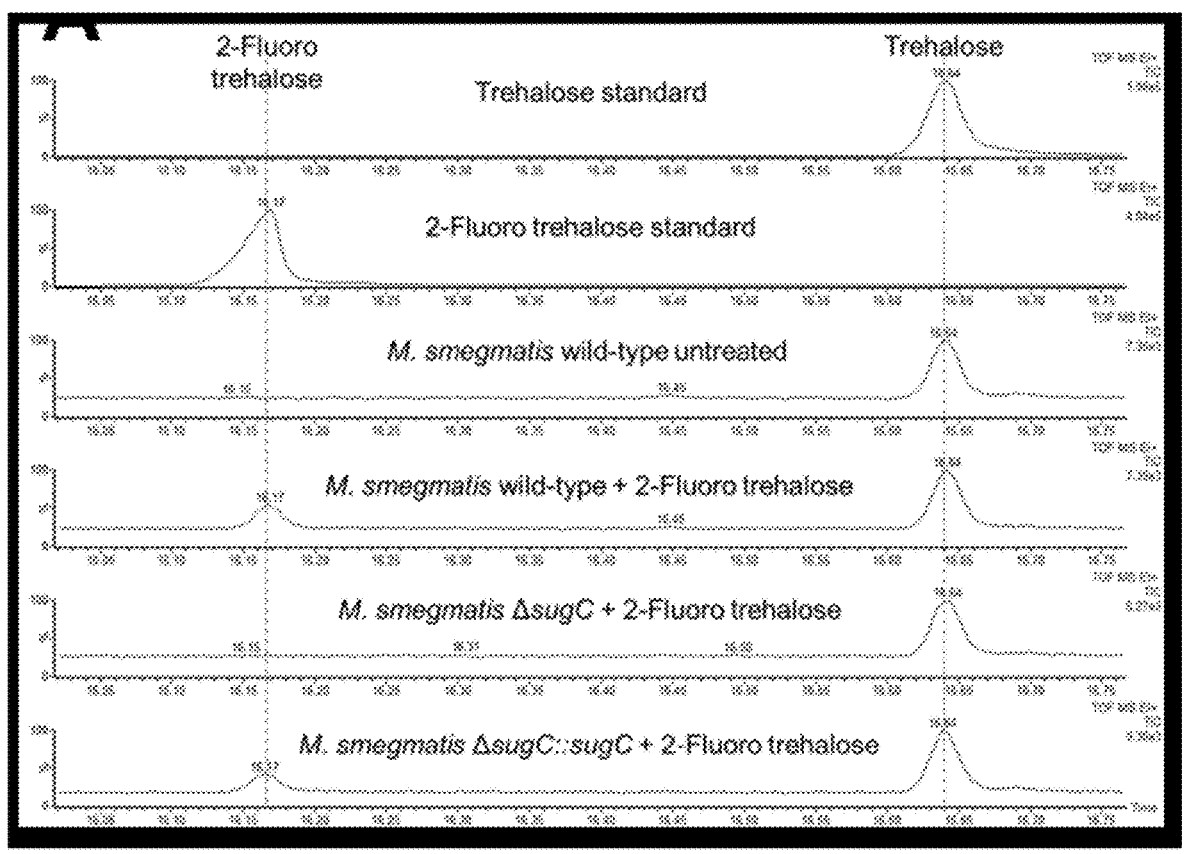
FIG. 3A, FIG. 3B, FIG. 3C, FIG. 3D, and FIG. 3E.
Figure 3B:
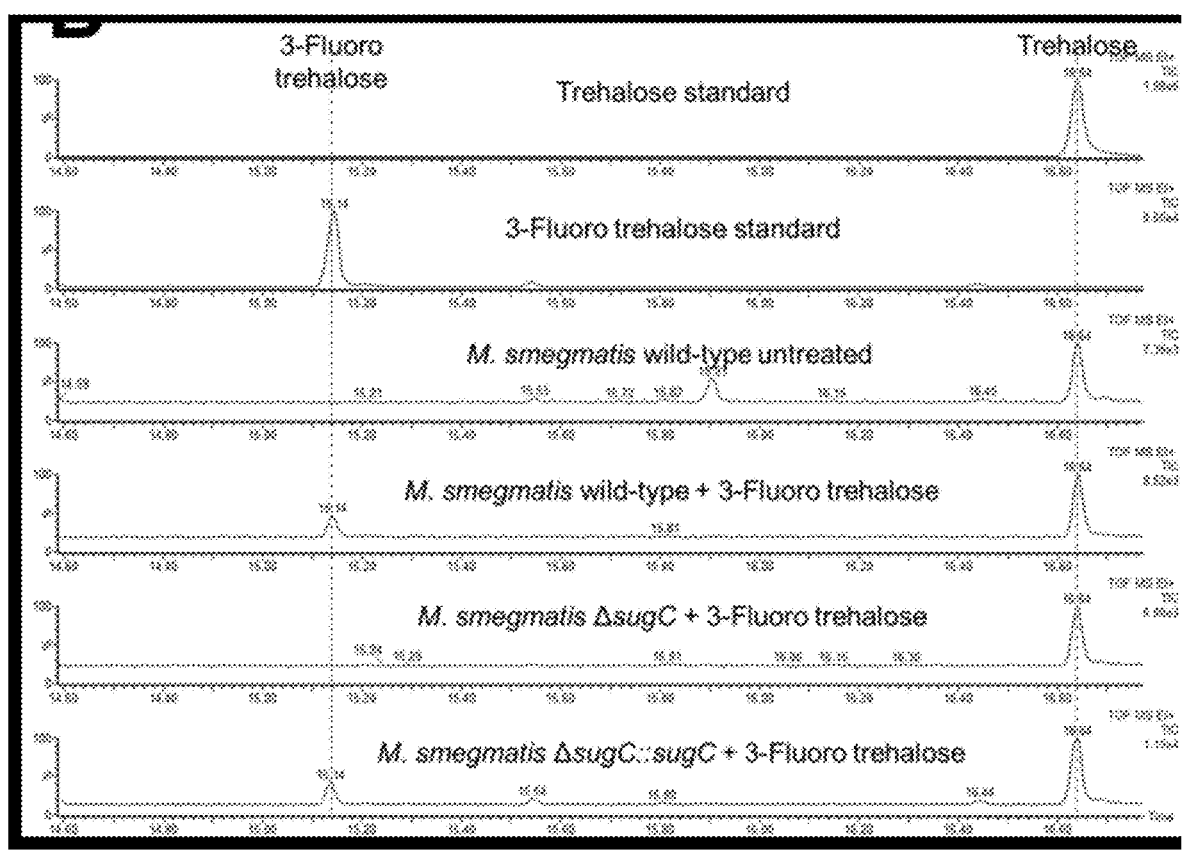
Figure 3C:
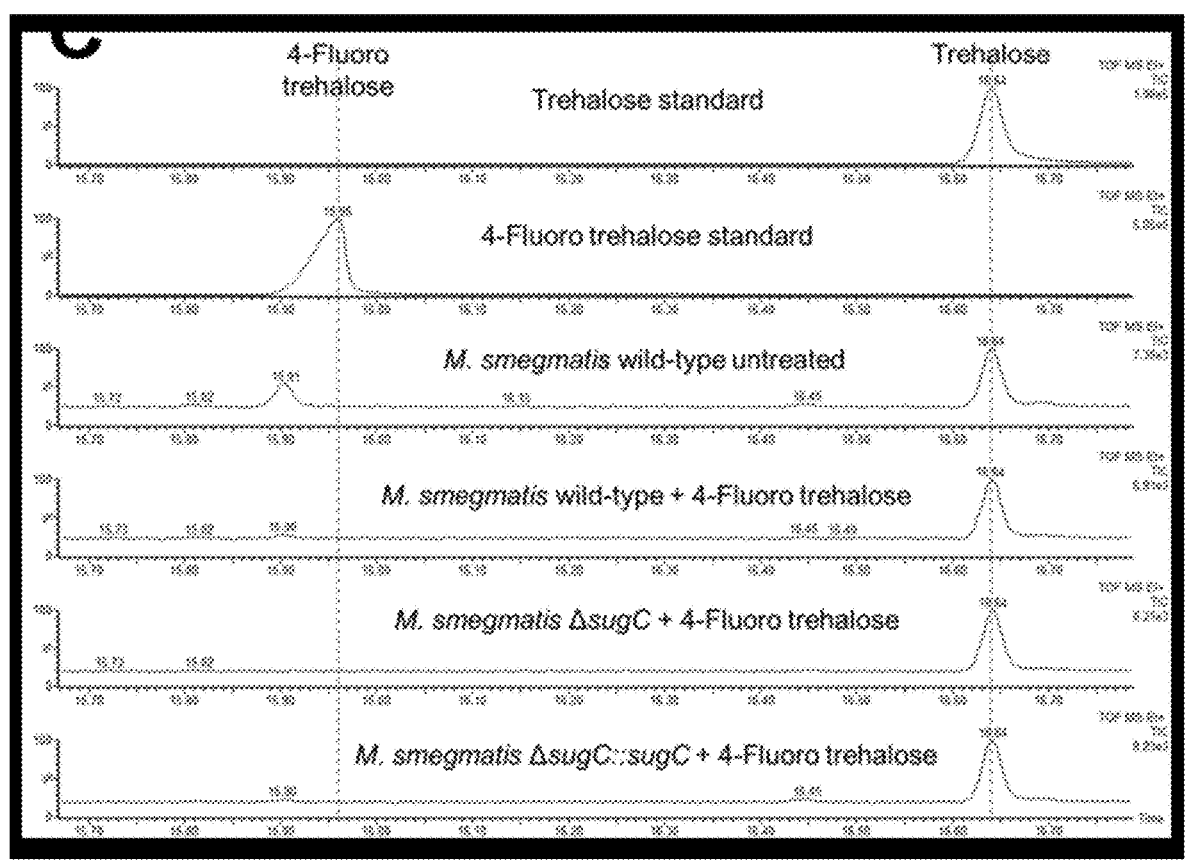
Figure 3D:
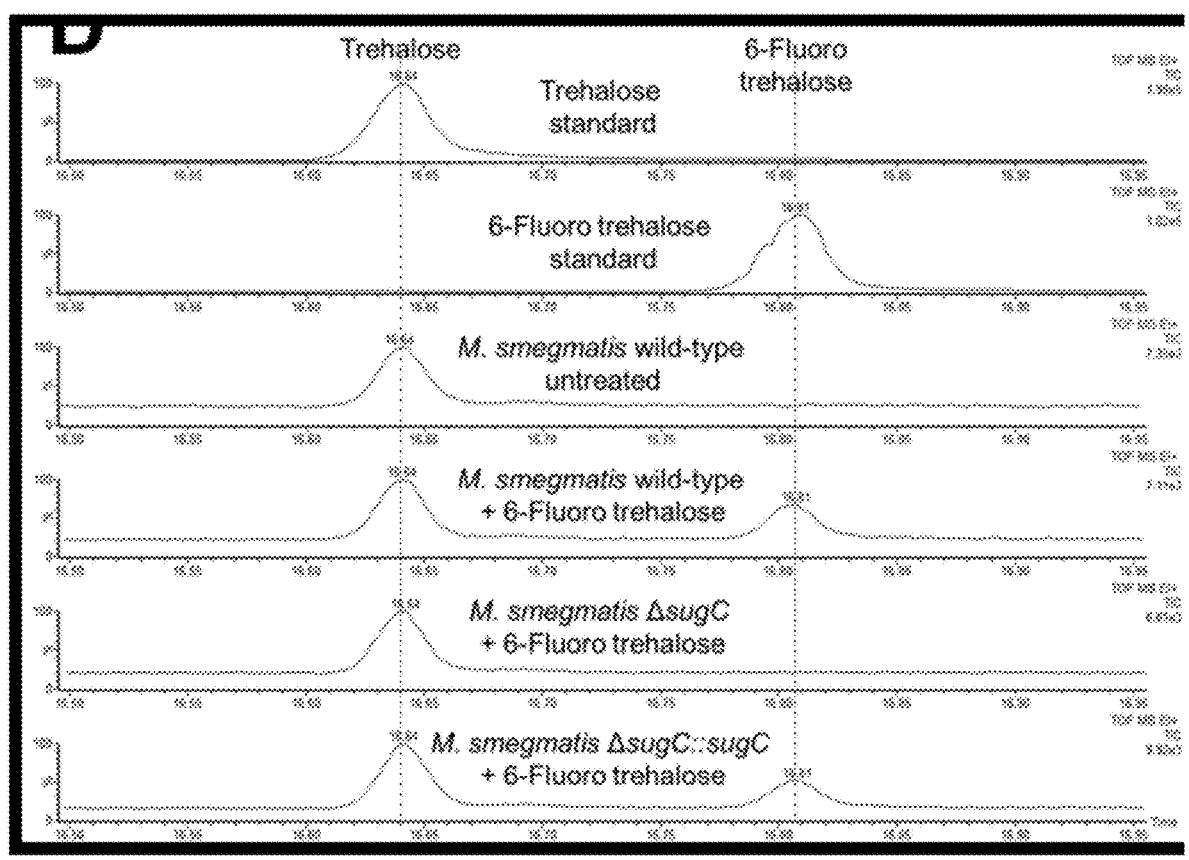
Figure 3E:
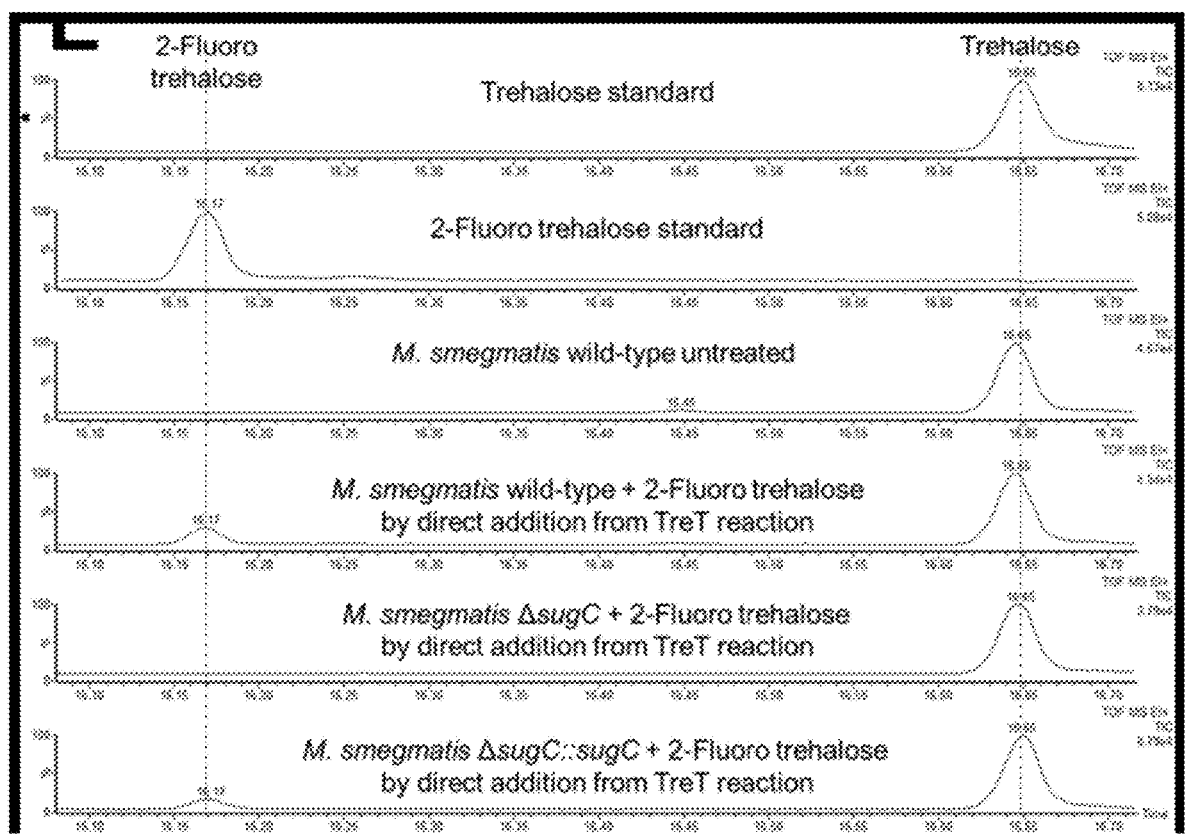

FIGS. 3A-3D show gas chromatograms for uptake of purified 2-, 3-, 4-, and 6-fluoro trehalose. The corresponding fluoro trehalose derivative was observed in cytosolic extracts from wild-type *M. smegmatis* treated with 2-, 3-, and 6-fluoro trehalose, but not 4-fluoro trehalose. No uptake was observed for any analogues in the *M. smegmatis* ΔsugC mutant, while uptake was restored for each analogue in the ΔsugC::sugC complement. These data indicate that uptake of the fluoro trehalose analogues by mycobacteria is dependent on the trehalose transporter SugABC-LpqY. FIG. 3E shows gas chromatograms in a similar experiment, but in this case the 2-fluoro trehalose synthesized and administered using the rapid "one-pot metabolic labeling" method described above. Therefore, fluoro trehaloses can be rapidly synthesized by TreT in 60 minutes and immediately administered to mycobacteria, where they can selectively accumulate in the cytosol via the trehalose transporter.

In summary, Examples 1-4 demonstrated that the thermostable trehalose synthase TreT from *T. tenax* converted a broad variety of Glc analogues into trehalose analogues in a single step in high yield (up to >99%) in 1 h. The TreT reaction was biocompatible and rapid (i.e., 1 h), and thus, allowed for administration of trehalose-based chemical probes to mycobacteria and imaging of mycobacteria with no effect on bacterial growth or appearance. Accordingly, probe synthesis, metabolic labeling, and imaging of the mycobacteria was accomplished in a single day.

Various features and advantages of the invention are set forth in the following claims.

What is claimed is:

1. A compound according to formula (III) or (IV)

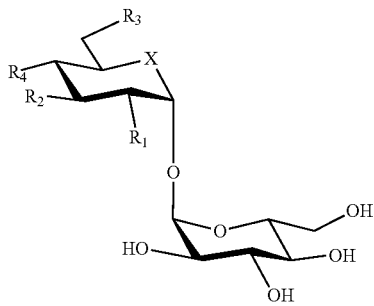
(III)

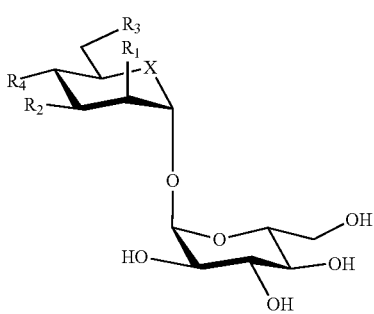
(IV)

wherein
X is S, Se, PH, P(O)H, or P(O)OH;
$R^1$, $R^2$ and $R^3$ are independently H, F, —OR, —SR, —SCOR, —OSO$_3^-$, —SeR, —SeCOR, —N$_3$, —CN, —NC, C$_{1-6}$ alkyl, C$_{2-6}$ alkenyl, or C$_{2-6}$ alkynyl;
$R^4$ is OH, —NHR, —SH, or —SeH; and
each R is independently H, C$_{1-6}$ alkyl, C$_{2-6}$ alkenyl or C$_{2-6}$ alkynyl.

2. The compound according to claim 1 that is

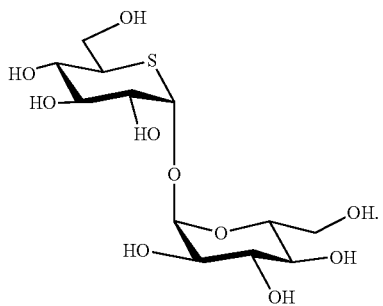

5-ThioTre

3. The compound according to claim 1, wherein the compound has formula (III).

4. The compound according to claim 1, wherein the compound has formula (IV).

5. The compound according to claim 1, wherein X is S.

6. The compound according to claim 5, wherein the compound has formula (III).

7. The compound according to claim 5, wherein the compound has formula (IV).

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: Mycobacterium smegmatis

<400> SEQUENCE: 1
tttttttaat taaatggccg aaattgtgtt ggatcg    36

<210> SEQ ID NO 2
<211> LENGTH: 33
<212> TYPE: DNA
<213> ORGANISM: Mycobacterium smegmatis

<400> SEQUENCE: 2
tttttaagct tcacccggcg tccggccccg ccg    33